(12) United States Patent
O'Donoghue

(10) Patent No.: US 8,460,298 B2
(45) Date of Patent: Jun. 11, 2013

(54) SURGICAL BUR WITH UNEQUALLY SPACED FLUTES, FLUTES WITH DIFFERENT RAKE ANGLES AND FLUTES WITH ALTERNATING RELIEFS

(75) Inventor: Denis O'Donoghue, Killarney (IE)

(73) Assignee: Stryker Ireland Ltd., County Cork (IE)

( * ) Notice: Subject to any disclaimer, the term of this patent is extended or adjusted under 35 U.S.C. 154(b) by 1007 days.

(21) Appl. No.: 12/191,405

(22) Filed: Aug. 14, 2008

(65) Prior Publication Data

US 2009/0048602 A1 Feb. 19, 2009

Related U.S. Application Data

(60) Provisional application No. 60/955,890, filed on Aug. 15, 2007.

(51) Int. Cl.
*A61B 17/00* (2006.01)
(52) U.S. Cl.
USPC .......................................................... 606/80
(58) Field of Classification Search
USPC 606/79, 80, 172; 433/165–166; 408/227–230
See application file for complete search history.

(56) References Cited

U.S. PATENT DOCUMENTS

| | | | | |
|---|---|---|---|---|
| 265,998 | A | * | 10/1882 | Valentine ...................... 408/229 |
| 788,906 | A | * | 5/1905 | Homann ....................... 433/165 |
| 4,740,121 | A | * | 4/1988 | Arnold .......................... 408/224 |
| 5,312,208 | A | * | 5/1994 | Shiga et al. ................... 408/224 |
| 5,888,200 | A | * | 3/1999 | Walen ............................ 606/167 |
| 6,379,090 | B1 | * | 4/2002 | Halley et al. .................. 408/227 |
| 6,547,495 | B2 | * | 4/2003 | Meece et al. ................. 408/1 R |
| 6,562,055 | B2 | | 5/2003 | Walen |
| D536,095 | S | * | 1/2007 | May ............................. D24/146 |
| 7,207,752 | B2 | * | 4/2007 | Schulte ......................... 408/224 |
| 2008/0132929 | A1 | | 6/2008 | O'Sullivan et al. |

* cited by examiner

*Primary Examiner* — Nicholas Woodall

(57) ABSTRACT

A surgical bur including a shaft with a head on the distal end of the shaft. A number of flutes extend outwardly from the head, each flute having a rake surface and a clearance surface. On some flutes the rake and clearance surfaces meet to form the flute cutting edges. Other flutes have relief surfaces between the rake and cutting surfaces. On these flutes, the cutting edges are the edges where the rake and relief surfaces meet. The flutes are further designed to have rake angles that are less negative, than the flutes without the relief surfaces. The flutes are radially spaced apart around the head such that between any three adjacent flutes, the first and second flutes are spaced apart a first angle; the second and third flutes are spaced apart a second angle different from the first angle.

25 Claims, 3 Drawing Sheets

SURGICAL BUR WITH UNEQUALLY SPACED FLUTES, FLUTES WITH DIFFERENT RAKE ANGLES AND FLUTES WITH ALTERNATING RELIEFS

This application claims priority from U.S. Provisional Pat. App. No. 60/955,890 filed 15 Aug. 2007. The contents of this application are incorporated herein by reference.

FIELD OF THE INVENTION

This invention is generally related to surgical burs. More particularly, this invention is related to a surgical bur with flutes that are both non-uniform in shape and that have varying inter-flute separations to reduce chatter when the bur is applied to a surgical site.

BACKGROUND OF THE INVENTION

One cutting accessory used to perform a surgical procedure is the bur. A bur generally consists of a head formed from rigid material, typically metal, shaped to have a number of flutes. The flutes are formed to define cutting edges. More particularly, the flutes are typically designed to cut hard tissue, such as bone or cartilage. A shaft extends rearwardly from the head. The proximal end of the shaft often has a feature that facilitates locking the shaft to a powered handpiece. The actuation of the handpiece results in the rotation of the bur. During a surgical procedure, the bur head is placed against a surgical site where a section of tissue is to be removed. The rotating cutting edges excise tissue away from the surgical site. Burs of various shapes and sizes are used in procedures such as orthopedic surgery, neuro and spinal surgery, ear noise and throat surgery and in other surgical procedures in which a sub-procedure is to selectively remove a section of tissue.

Burs work well for the purposes for which they are designed. Nevertheless, a problem associated with some burs is chatter. Chatter is the back and forth vibration of a bur head against the surface to which the bur head is applied. Chatter occurs as a result of bur's individual cutting edges repeatedly being forced against the tissue against which the bur head is applied. There are a number of reasons a bur may chatter.

One reason a bur chatters is because it receives an input of energy due to a process known as regeneration of waviness. This process is due to the fact that, when a cutting edge passes across a section of tissue, it leaves a specific wavy (essentially sinusoidal) profile along the surface of the tissue. If two adjacent cutting edges cut in phase, the second cutting edge excises tissue along a surface profile identical to that along which in was excised by the first flute. In practice, due to the invariable movements of the bur head and the tissue, this does not happen. When any two successive cutting edges pass over the same tissue section, the second flute cutting edge removes tissue on a path that does not overlap the tissue wave formed by the chip excised by the first cutting edge. Consequently, the debris chips cut by the second cutting edge have variable thicknesses. This means, during the process in which the second cutting edge excises the chip from the tissue, the cutting edge and its flute are subjected to variable forces. Over time, the repetitive exposure of the bur flutes to these variable forces causes the bur to undergo forced vibration. This vibration results in bur chatter.

The Applicant's Patent Application U.S. Pat. Pub. No. 2008/0132929 A1, the contents of which are incorporated herein by reference, discloses a bur with flutes designed to reduce chatter. The bur of this invention includes multiple flutes. More particularly, this bur is shaped so that some, but not all, of the flutes are formed so that their cutting edges emerge from the body the bur head very close to the distal end tip of the bur head. The remaining flutes are shaped so that their cutting edges emerge from the bur head at positions more proximal to the distal end tip of the bur head. This bur has been found to be somewhat effective in reducing bur chatter.

Nevertheless, even a bur constructed with the above features can, in some circumstances, chatter.

SUMMARY OF THE INVENTION

This invention is directed to a new and useful surgical bur. The bur of this invention is provided with flutes that have both non-uniform shapes and that are arcuately spaced apart from each other by different angles.

One feature of the bur of this invention is that the flutes are arranged so that at least one pair of arcuately adjacent flutes are spaced apart a first angle from each other while another pair of arcuately adjacent flutes are spaced apart from each other a second angle different from the first angle. In some versions of the invention, the flutes are arranged so that the flutes forming each pair of adjacent flutes are spaced apart from each other a different angle than the flutes forming the adjacent pairs of flutes. In some versions of the invention, the flutes are arranged in at least two sets. Within each set of flutes, the flutes are angularly spaced apart from each other a first maximum angle. Collectively, the sets of flutes are forming each adjacent set of flutes are spaced apart from each other an angle greater than the largest intra-set maximum flute separation angle.

The bur of this invention is further constructed so that at least two flutes have different rake angles. In some versions of the invention, the bur is constructed so that the flutes with have two rake angles and the rake angles of the flutes alternate with each other. Also, some burs of this invention are constructed so that each flute has a negative rake angle.

It is still another feature of the bur of this invention that some, but not all of the flutes are formed with relief surfaces. This relief surface, when present on a flute, extends between the rake surface and the clearance surface. Thus, the edge between the rake surface and a relief surface of a flute forms the cutting edge of the flute. In some versions of the invention, the flutes are formed in an alternating pattern wherein a first flute does not have a relief surface however the adjacent flute does have a relief surface.

BRIEF DESCRIPTION OF THE DRAWINGS

The invention is pointed out with particularity in the claims. The above and further features of this invention may be better understood by reference to the following detailed description taken in conjunction with the accompanying drawings in which:

DETAILED DESCRIPTION

Figure 1:
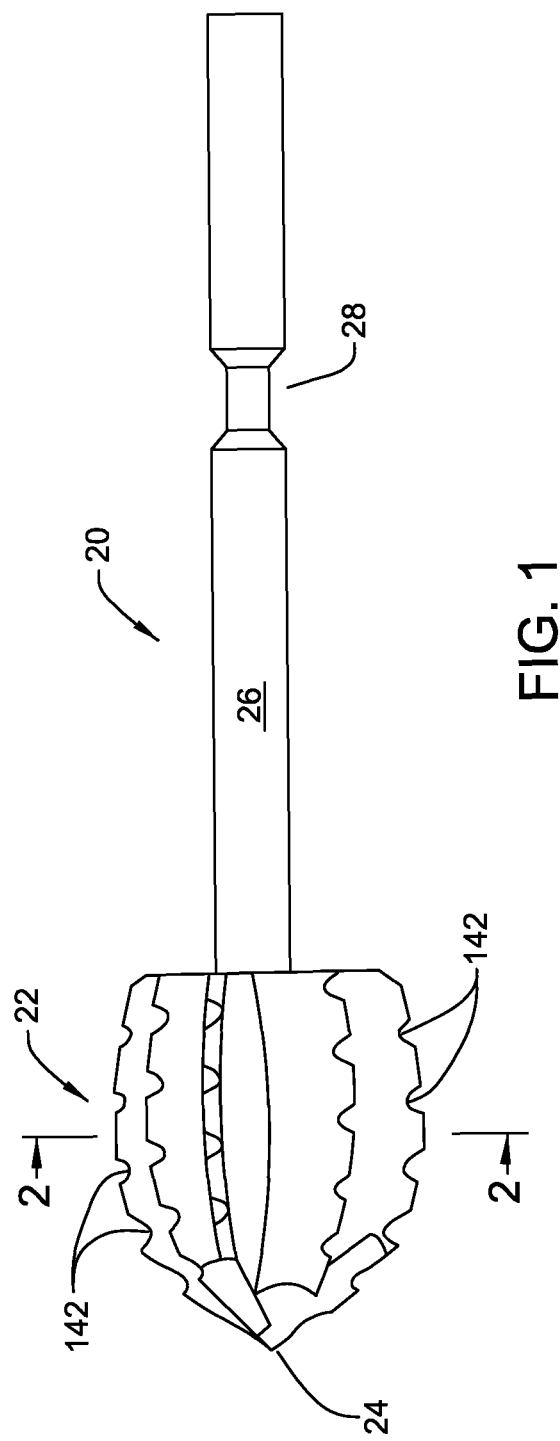
FIG. 1 is a side view of a basic surgical bur constructed in accordance with this invention.

FIG. 1 illustrates a surgical bur 20 constructed in accordance with this invention. Bur 20 has a head 22 that forms the distal end of the bur. ("Distal" it shall be understood, means towards the surgical site to which the bur is applied. "Proximal" means away from the surgical site.) Bur head 22 has a distal end tip 24 that is the most forward portion of the bur 20. A shaft 26 extends proximally rearward from the bur head 22.

In many versions of this invention, bur 20 is designed to perform neurological, ENT, spinal or orthopedic surgical procedures. Accordingly, in many versions of the invention bur head 22 has a maximum outer circumference of 15 mm or less. In other versions of the invention, the maximum outer circumference of the bur head 22 is 10 mm or less.

The proximal end of the shaft 26 is provided with coupling features 28. The coupling features 28 are geometric features that facilitate the removable engagement of the shaft 26 to a coupling assembly integral with the rotating shaft of a powered surgical tool with which bur 20 is used (tool not illustrated.) The illustrated coupling features 28 are a set of planar faces recessed relative to the outer diameter of the shaft 24. One such geometry is described and illustrated in U.S. Pat. No. 5,888,200, issued 30 Mar. 1999, Multi-Purpose Surgical Tool System, the contents of which is incorporated herein by reference. An alternative geometry for coupling features 26 in the form of linearly aligned opposed concave surfaces is illustrated in U.S. Pat. No. 6,562,055, issued 13 May 2003, Cutting Attachment For A Surgical Handpiece Designed To Be Selectively Coupled To The Handpiece, the contents of which is incorporated herein by reference. It should be appreciated that these two geometries of coupling features are exemplary, not limiting. In alternative versions of the invention, these coupling features may for example, be threading. Alternatively, tabs that project outwardly from the outer surface of shaft 24 may function as the coupling features. In some versions of the invention, the coupling feature 28 may simply be a section of the smooth walled shaft 24 against which the fingers of a tool chuck bear to hold the bur 20 to the tool. Thus, the exact geometry of the coupling feature is not relevant to the structure of this invention.

Figure 2:
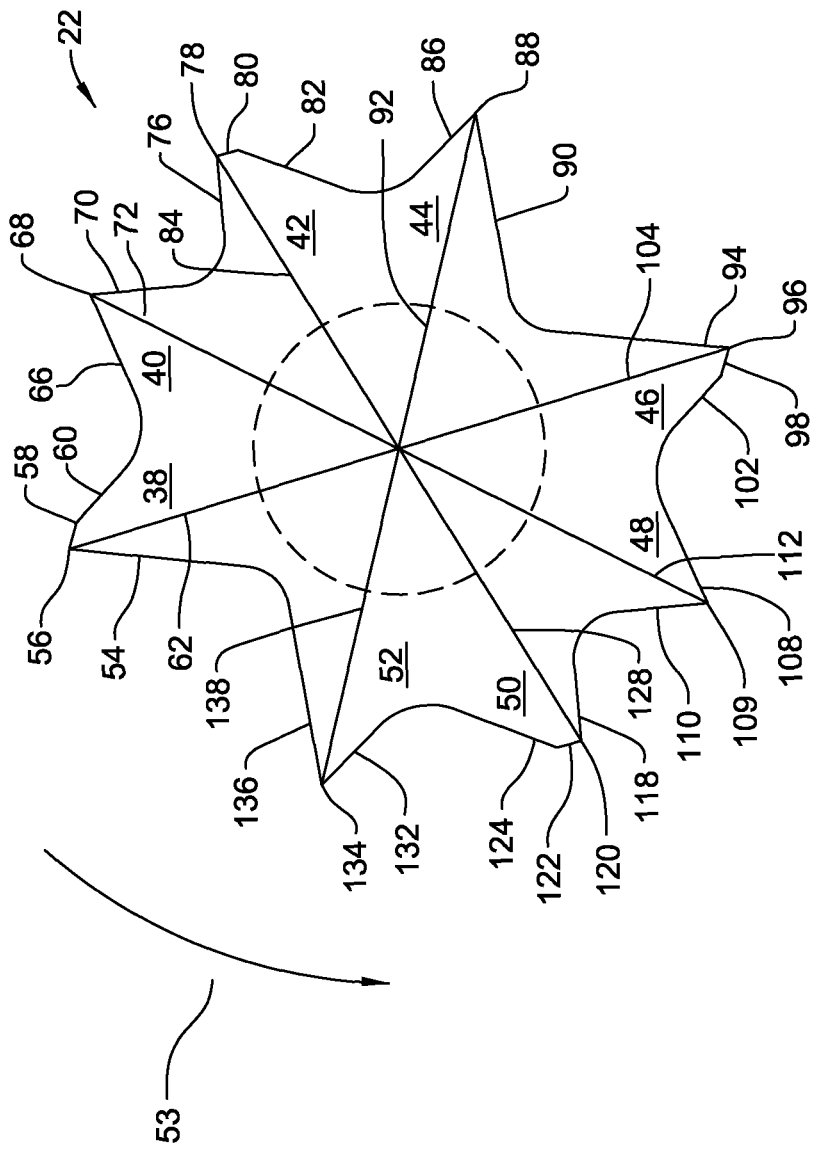
FIG. 2 is a cross sectional view of the perimeter of the flute of this invention taken along line 2-2 off FIG. 1.

A number of arcuately spaced apart flutes 34-52, best seen in FIG. 2, extend radially outwardly from bur head 22. In FIG. 2 curved arrow 53 is provided to represent that the bur head 22 rotates counterclockwise. Generally, each flute 34-52 is formed to have a rake surface and a clearance surface. The rake surface is the surface of the flute that, as the flute rotates, strikes the bone against which the flute is applied. The outer perimeter, the outer edge, of each rake surface is the actual cutting edge of the flute. Each flute 34-52 is further formed so as to have a side surface opposite the rake surface; this is the clearance surface. Some flutes of the bur of this invention are formed so that the clearance surface is the surface that abuts the rake surface to form the cutting edge. Other flutes of this invention are further formed to have a relief surface. The relief surface extends rearwardly from the cutting edge. (Here "forwardly" is understood to mean in the direction of rotation of the bur head. "Rearwardly" is understood to mean opposite the direction of rotation of the bur head.) The tail end of the relief surface, when present, abuts the forward edge of the clearance surface with which the relief surface is integral.

In more detail, it can be seen that flute 38 is formed to have a rake surface 54, a relief surface 58 and a clearance surface 60. Point 56, where the rake surface 54 and relief surface 58 intersect, represents the cutting edge of flute 38. In the illustrated version of the invention, rake surface 54 is formed so that after the surface initially curves away from its position closest to the axis of rotation and extends to the cutting edge, the surface has a linear profile. The other rake surfaces have similar curve-into-line profile geometry. In FIG. 2, a radial line 62 is shown extending from the longitudinal center axis of the bur head 22 to the cutting edge.

Flute 38 is further shaped so as to have a negative rake angle. In other words, the flute 38 is shaped so that, forward from the cutting edge, the rake surface 54 extends in front of the radial line 62 that extends to the cutting edge. In one version of the invention, this angle, measured around the point where the radial line 62 extends inwardly from the cutting edge 56, is between −25° and 0°. (The angle is referred to as a "negative" angle because the flute has a "negative" rake surface. A rake surface coincident with the associated radial line has a rake angle of 0°) It should be understood that this angle is the angle of the section of the rake surface 38 immediately forward of the cutting edge. Forward of this section of the rake surface, since the rake surface continues to curve forward, the rake angle increases.

Relief surface 58, which is generally planner, extends rearward from the cutting edge of flute 38. More particularly, relief surface 58 is at an angle, relative to its intersection with radial line 62, that is between approximately 50 to 80°. In other versions of the invention, this angle is between 70 and 80°. Clearance surface 60 is angled inwardly from the rear end of the relief surface 58. Here "angled inwardly" means that the slope of the line along which clearance surface 60 lies relative to the cutting edge tangent line is greater than the slope of the relief surface 58.

Flute 40 is the flute located immediately rearward of flute 38. Bur 20 is formed so that flute 40 has a rake surface 66 and a clearance surface 70. Point 68, where surfaces rake and clearance surfaces 66 and 70, respectively, intersect, represents the cutting edge of flute 40. Line 72 represents the radial line from the center axis of the bur head 22 to the cutting edge of flute 40. Bur 20 is formed so that the rake surface 66 begins adjacent where clearance surface 60 of flute 38 terminates. Not identified is the curved surface that is the transition between clearance surface 60 and rake surface 66. The bur 20 is further formed so that rake surface 66 provides flute 40 with a negative rake angle. This negative rake angle is more negative than the negative rake angle of flute 38. In some versions of the invention, the negative rake angle of flute 40, the angle between radial line 72 and the surface of the rake surface 66 immediately forward of the flute cutting edge is between −45° and 0°. Clearance surface 70 has a curved profile that, rearward of the flute cutting edge, extends inwardly.

Rearward from flute 40, bur 20 is formed to define flute 42. Bur head 22 is shaped so that flute 40 has a rake surface 76, a relief surface 80 and a clearance surface 82. The intersection of the rake surface 76 and relief surface 80, point 78 in FIG. 2, is the cutting edge of flute 42. Radial line 84 extends from the center of the bur head to the cutting edge of flute 40. The bur is formed so that rake surface 76 curves outwardly from the rear terminus of clearance surface 70. Also, the bur is shaped so that rake surface 76 provides flute 42 with the same negative rake angle associated with flute 38. Relief surface 80 extends away from the tangent line associated with the cutting edge of flute 42 by the same degree with which relief surface 58 extends away from the cutting edge tangent line with which surface 58 is associated. Clearance surface 82 has the same profile as the clearance surface 60 integral with flute 38.

Bur head 22 is further formed so, at the rear terminus of clearance surface 82, there is an upward curve, (not identified). This curve forms that transition into a rake surface 86 of flute 44. More particularly, flute 44 is formed so that rake surface 86 has a profile identical to that of rake surface 66 of flute 40. A clearance surface 90 extends rearwardly from rake surface 84. Point 88, located at the junction of rake surface 86 and clearance surface 90, represents the cutting edge of flute 44.

Radial line 92 extends between the center of the bur 20 and the cutting edge of flute 44. Given that rake surface 86 is identical to rake surface 66 of flute 40, flute 44 has the same negative rake angle of flute 40.

Bur 20 of this invention is further constructed so that flutes 38, 40, 42 and 44 are not equangularly spaced apart from each other. In some versions of the invention, flutes 38 and 40 are spaced apart from each other, have a pitch angle of, between 40 and 60°. This angle is understood to be the angle between the radial line 62 associated with flute 38 and radial line 72 associated with flute 40. The pitch angle between flutes 40 and 42 is less than the pitch angle between flutes 38 and 40. In some versions of the invention, the pitch angle between flutes 40 and 42 is between 24 and 40°. This angle is the angle between radial line 72 and radial line 84 of flute 42. Flutes 42 and 44 are positioned relative to each other so that there angular separation is equal to the angular separation between flutes 38 and 40. Here, the pitch angle is between radial line 84 and radial line 90.

Bur 20 is also formed so that flutes 38-44 form a first set of flutes and flutes 46-54 form a second set of flutes. The two sets of flutes are equangularly spaced apart from each other at pitch angle greater than the pitch angle separating any two flutes within a set of the flutes. Also, bur 20 is formed so that the flutes 46-54 are reverse symmetric relative to flutes 38-42.

Owing to the above features of bur 20, flute 44 has a clearance surface 90 that is at an angle relative to the associated radial line 92 that is more acute than the angles between the clearance surfaces of flutes 38, 40 and 42 and their associated radial lines. This clearance surface 86 curves into the surface forming rake surface 94 of flute 46. Flute 46 is identical to but in reverse orientation to flute 38. Therefore, rake surface 94 has a shape that is reverse symmetric to that of rake surface 54 of flute 38. Flute 46 is further formed with a relief surface 98 and a clearance surface 102 that are reverse symmetric to, respectively, surfaces 58 and 60 flute 38. Point 96, the intersection of rake surface 94 and relief surface 98 represents the cutting edge of flute 46. Radial line 104 extends from the center of the bur to the cutting edge of flute 46. Thus, by point of reference, flutes 38 and 46 are reverse symmetric with respect to the line extending between the cutting edges of these flutes. This line is the combination of radial lines 62 and 104

Continuing, flute 48, the flute rearward of flute 46, is reverse symmetric with respect to flute 40. Accordingly, flute 48 has a rake surface 108 that corresponds to rake surface 66 and a clearance surface 110 that corresponds to clearance surface 70. Radial line 112, which extends to the cutting edge of flute 48, point 109 in FIG. 2, is collinear with radial line 72. Flute 50 is therefore reverse symmetric with respect to flute 42. Therefore, flute 50 is formed with a rake surface 118, a relief surface 122 and a clearance surface 124. These surfaces 118, 122, and 124 correspond, respectively to surfaces 76, 80 and 82 of flute 42. A radial line 128 extends to the cutting edge of flute 50. Line 128 is collinear with radial line 84. Line 128 terminates at the cutting edge of flute 50, point 120 in FIG. 2.

Flute 52 is the last-described flute of bur 50. Flute 52 is reverse symmetric with respect to flute 44. Accordingly, flute 52 has a rake surface 132 and a clearance surface 136. Point 134 represents the cutting edge of flute 52. Surfaces 132 and 136 are, accordingly, reverse symmetric with respect to, respectfully rake surface 88 and clearance surface 90. Radial line 138, which extends to the cutting edge of flute 52 is collinear with radial line 92. Owing to the reverse symmetry of the bur 20, the clearance surface 136 of flute 52 curves into the rake surface 54 of flute 38.

Given the reverse symmetry of bur 20, the angular separation of between adjacent flutes 46 and 48 and adjacent flutes 50 and 52 are equal. This angular separation is, however, less than angular separation between adjacent flutes 48 and 50.

Also, as discussed above, the two sets of flutes, flutes 38-44 and flutes 46-52, are equangularly spaced apart from each other, the pitch angle between the sets of flutes is larger than the pitch angle between any two adjacent flutes within one of the sets of flutes. Thus in some versions of the invention, the pitch angle between flutes 44 and 46, which is also the pitch angle between flutes 38 and 52, is between 45 and 90°. In many versions of the invention, this angle is between 47 and 57°. Owing to the above arrangement of the flutes 38-52, it will be appreciated that, in the described version of the invention the pitch angle between any pair of arcuately adjacent flutes is different, varies, from the angle between the pairs of arcuately adjacent flutes on either side of the initial pair of flutes.

Still another feature of the bur 20 of this invention is that flutes 38-54 are each formed with a number of gashes 142, best seen in FIG. 1. The gashes 142 are longitudinally spaced apart from each other along the length of the flute in which they are formed. The most distal located 142 gash is located proximal to the relief surface of the flutes 38, 42 46 and 50 formed with relief surfaces.

Figure 3:
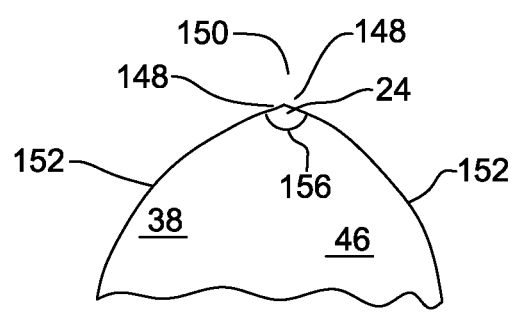
FIG. 3 is an enlarged illustration of the tip of the bur.

Bur 20 is formed so that immediately proximal to tip 24 all but two of the flutes are formed with gashes, Consequently only two of the symmetrically aligned flutes, flutes 38 and 46, meet to define the tip 24. Tip-defining flutes 38 and 46 are further formed so that their outer surfaces define plural curve (or line) edge segments. Specifically, as seen in FIG. 3, each flute 38 and 46 is shaped so that the associated cutting edges, cutting edges 56 and 96, respectively, each consists of a distal edge segment 148 and a proximal edge segment 152. Distal edge segments 148 meet to define the most distal end point 150 of the tip 24 and, by extension, bur 20. More particularly flutes 38 and 46 are formed so that distal edge segments 148 provide the tip 24 with an obtusely acuminate profile. In other words, distal edge segments 148 taper to point 150 and are further shaped so that relative to each other edge segments 148 are at an angle to each other, with tip 24 as a vertex, of at least 90°. In the Figures, this angle is exaggerated for purposes of illustration. At approximately the position along the length of the bur the cutting edges of the remaining flutes 40, 42, 44, 48, 50 and 52 emerge, flutes 38 and 46 are formed so that the proximal edge segments 152 extend proximally from the distal edge segments 152. These proximal edge segments 152 have the same convex, outwardly curved, profile of the adjacent flutes.

In the illustrated version of the invention, distal edge segments 148 are shown as curving forwardly and inwardly away from proximal edge segments 152 to meet at point 150. It should be appreciated that the apparent angle of edge segments 148 relative to each other should be considered an "apparent" obtuse angle at the most proximal position of the edge segments 148 at their most distal location relative to point 150. This is represented by arc 156 in FIG. 3.

Bur 20 of this invention is used in a manner similar to that in which conventional burs are used. Shaft 26 is inserted in a tool and rotated. A coupling assembly integral with the tool engages the shaft coupling features 28 so the bur shaft 26 will rotate with the tool shaft. The rotation of the shaft 26 results in a like rotation of the bur head 22. The bur head 22 and, more particularly, the eight flutes 38-54, are pressed against the tissue, the bone, to be cut. As each rake surface rotates against the tissue, it removes, it cuts away at least a portion of the section of the tissue immediately in front of it.

As discussed above, the pitch angles between a first flute and the following second flute is different from pitch angle between the second flute and the following third flute. Accordingly, in the successive removal of bone by the successive flutes, substantially identical sections of bone are not removed by the flutes. Instead, sections of bone of different lengths are removed. This non-uniform removal of bone substantially eliminates the pattern of a waves forming on the remaining bone. The reduction in this waviness of remaining bone minimizes the chatter that can otherwise occur when, in additional pass of the bur head 22, the flutes again strike the bone.

Bur chatter is likewise reduced as a consequence of the flutes having different rake angles. Specifically, the amount of force each a flute places against the surface, the bone, against which the flute is pressed is a function of the rake angle. Generally, the more negative the rake angle the greater the force against bone. Bur 20 of this invention is designed so that successive flutes have different rake angles. Therefore, this variation in rake angles therefore further varies the force each flute imposes against the bone. This further minimization of the constant flute striking against the bone at a constant force further reduces the incidence of bur chatter.

Bur 20 is further designed so that flutes 38, 42, 46 and 50, the flutes with the less negative, more positive, rake angle are provided with relief surfaces. The presence of these relief surfaces provides these flutes with, around their cutting edges, a relatively large flute tip angle. Owing to these flutes 38, 42, 46 and 48 having a relatively large flute tip angle these flutes tend to make shallow bites into the bone against which they are applied. This is in contrast to flutes 40, 44, 48 and 52. Given the absence of relief surfaces integral with flutes 40, 44, 48 and 52, these flutes have a relatively small flute tip angle around their cutting edges. The relatively small flute tip angle around these cutting edges means that when flutes 40, 44, 48 and 52 strike bone, they tend bite relatively deeply into the bone.

Thus, with bur 20 of this invention, the flutes engage in a deep bite/shallow bite/deep bite/shallow bite pattern of tissue removal against the bone. If the flutes where to engage solely in repetitive deep biting against the bone; the result would be the repetitive large energy strikes of the bur against the bone. Large energy strikes at high frequencies contribute to bur chatter. Also, in this invention, all the flutes do not repetitively engage in shallow biting against the bone. When a flute engages in shallow biting against the bone, the flute is in contact with the bone for a relatively long period of time, as opposed to when there is deep biting. When this shallow biting occurs, there is greater frictional force in opposition to the rotation of the bur (as opposed to the biting contact). Overcoming this force cause a greater amount of frictional heat to be generated. The generation of such heat can cause damage to the bone. However, in this invention, flutes 40, 44, 48 and 52 do not present these relief surfaces against the bone. Therefore, less frictional force is encountered, and less heat generated, than if all of the flutes were formed with relief surfaces.

Thus, the bur 20 of this invention is provided with flutes that both minimize bur chatter and the heat that could otherwise develop due to the presence of the feature that eliminates the chatter.

Furthermore, the lack of relief surface rearward of the cutting edges of flutes 40, 44, 48 and 52 increases the size of the void spaces behind these flutes. (This is in comparison to the void spaces behind flutes 38, 42, 46 and 50.) Consequently, relatively large volumes of bone chips can be temporarily held in the void spaced behind flutes 40, 44, 48 and 52. The ability of these void spaces to hold large volumes of chips reduces the friction force these chips apply to the uncut bone as they are rotated against this bone. The reduction in this friction reduces the extent this force burns or otherwise heat scars the surface of the uncut bone.

The gashes 142 minimize the extent to which relatively long sections of bone are, in any rotation of a single flute against the bone, cut. The formation of small sized bone chips minimizes the force, reduces the effort required to force these chips away from the site to which the bur head is applied.

The features of the illustrated version further make bur 20 well suited for use for forming a bore in the skull. In many neurological surgical procedures, the formation of this bore is one of the initial steps performed. This bore is formed as part of the process of removing a section of the skull in order to gain access to the underlying section of the tissue on which the procedure is to be performed. Immediately underlying the skull is the dura. The dura is membrane that serves as a cushion between the brain and skull. When a bore is formed in the skull care must be taken not to damage the underlying dura.

Figure 4:
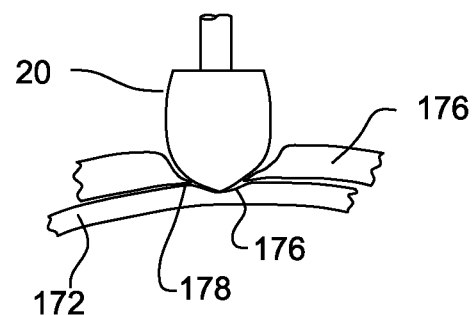
FIG. 4 is a side view illustrating how a bur of this invention is employed to form a bore in the skull.

Bur 20 of this invention can be used to form the bore into the skull. When the bur 20 starts to break through the skull 170, the tip 24 is actually the first section of the bur to extend completely through as seen in FIG. 4. Owing to the fact that tip 24 is defined by only two of the flutes, there is an appreciable amount of chatter, a report, when the tip initially breaks through the skull. This report provides the surgeon both tactile and audible feedback that the skull has been penetrated. Based on this feedback, the surgeon knows that it is time cease applying forward pressure on the bur 20 so as to stop the movement of the bur head 22 towards the dura 172.

Moreover, typically, as a result of a bur penetrating the skull, the distal end of the bur typically engages in some contact with the dura 172. With bur 20 of this invention, only the two flutes 38 and 46 forming the tip engage in this contact. These two flutes push the dura away from the distal end sections of the surrounding flutes. In FIG. 4 this is represented by the concave indentation 176 in the upper surface of the dura 172. Since only two flutes engage in this contact, the dura 172 is subjected to less friction-induced heating than if all the flutes were to rub against the dura. Moreover, the surface area of the dura subjected to this contact, ideally the circumference defined by flute distal surfaces 148, is less than surface area that is abutted by flutes having a more conventional acorn-design. The minimization of this contact area likewise results in reduction in the extent to which the dura 172 is subjected friction-induced heating. This reduction in the frictional induced heating of the dura results in a like minimization to the damage of the dura such heating can cause.

As a result of the penetration of the skull by the bur tip 24 a small annular shelf 178 is formed around the tip-formed opening in the skull 170. Using the tactile feedback of resistance/no resistance, the surgeon can, with the tip 24 detect the presence/absence of this shelf 178. Where the shelf 178 is present, the surgeon can exert lateral force so that the tip forming flutes 38 and 46 remove the bone forming the shelf. In this manner, the bore into the bone can be widened to the appropriate circumference while risk of damage to the underlying dura 172 is reduced.

Bur 20 of this invention offers a similar advantage when performing a laminectomy. In this procedure, a section of the lamina over the spinal cord is removed. Once this section of bone is removed, bur tip 24 pushes the underlying ligament forward to prevent damage to the ligament. This, by extension, reduces the likelihood that the spinal cord, which is disposed under the ligament, will be damaged The foregoing description is directed to one specific version of the bur of this invention. Other versions of the bur of this invention may have different features.

For example, there is no requirement that each of the foregoing features be in all embodiments of this invention. Thus all versions of this invention are not are required to have flutes with both different rake angles or flutes that are spaced apart from each by different pitch angles. Similarly, there is no requirement that bur head be formed so that the some, but not all, flutes are provided with relief surfaces.

Likewise when a bur is provided with the features of this invention, there is no requirement that requirement the features be exactly as described. In other versions of the invention wherein the flutes are spaced apart from each other at different pitch angles, there is no requirement that every two adjacent flutes be angularly spaced apart from each other at an angle different than those on either side of the baseline pair. Likewise, there is no requirement that the bur head be formed so that the flutes are in arcuately spaced apart sets. In versions of the invention wherein the flutes are so patterned, the flutes may be in three or more sets that are arcuately spaced apart from each other. Thus there is no requirement that the pitch angles between the burs be in the large to medium to small to medium and then back to large as described with respect to the illustrated version of the invention.

Likewise, the bur may be constructed so that two or more consecutive flutes share a common rake angle followed by one or more flutes with a different rake angle. Furthermore in some versions of the invention some or all of the flutes of this invention may be formed to have either a neutral or positive rake angle. Likewise, some burs of this invention may be formed with flutes that have three or more different rake angles.

It should similarly be appreciated that it is not required that in all versions of the invention all or any of the flutes have negative rake angles. Likewise, in some versions of the invention, the flutes with the relief surfaces may have rake angles that are more negative, less positive, than the flutes without the relief surfaces. Similarly, in comparison to the pitch angles between other flutes, the pitch angle between a flute with a relief surface and the rearwardly adjacent flute may be greater than the pitch angle between other pairs of flutes.

Also, in some versions of the invention, two or more flutes without relief surfaces may be present between the flutes with relief surfaces. Likewise, a bur head of this invention may have two or more flutes with relief surfaces followed one or more flutes each without a relief surface. Also, in some versions of the invention, the profiles of the rake surfaces may be more curved that in the illustrated version.

Further, in the described version of the invention, the flutes are formed so that, at a cross sectional location along the length of the bur head the cutting edges lie on a common circle. This circle is centered on the center longitudinal axis of the bur 20; the axis around which the bur rotates. In some versions of the invention, the bur may be constructed so that at least immediately adjacent the bur tip, not all cutting edges are present along this same circle.

Also, in the illustrated version of the invention, bur head 22 is shown as having an acorn style shape; from the distal end tip, the head curves away from the longitudinal axis until reaching a crest, extending proximally from the crest the cross sectional profile of the bore decreases. This should understood to be only one example of the shape of the bur head and not limiting. Alternative versions of the invention include burs formed with heads that are spherical, cylindrical, conical, frusto-conical or a combination of two or more of these shapes.

In versions of the invention wherein the bur has an acorn profile, the acuminate tip that emerges from the acorn-defining arcs may not be present. In versions of the invention wherein this tip is present, the opposed edges that define this type may not be at an obtuse angle relative to each other.

Therefore, it is an object of the appended claims to cover all such variations and modifications that come within the true spirit and scope of this invention.

What is claimed is:

1. A bur for use with a surgical tool, said bur having:
   a shaft, said shaft formed with features to facilitate the coupling of the bur to a surgical tool capable of rotating said shaft and a distal end;
   a head located forward of the distal end of said shaft, said head formed with a plurality of flutes each said flute having: a rake surface with a rake angle; and a clearance surface, said plurality of flutes including:
      a first set of flutes, said flutes of said first set of flutes having a first rake angle; and
      a second set of flutes, said flutes of said second set of flutes having a second rake angle, the second rake angle being different from the first rake angle and
      wherein, said flutes are arranged on said head so that: said flutes forming a first pair of arcuately adjacent flutes are spaced apart by a first pitch angle; said flutes forming a second pair of arcuately adjacent flutes are spaced apart by a second pitch angle different from the first pitch angle; and said flutes forming a third pair of arcuately adjacent flutes are spaced apart by a third pitch angle, the third pitch angle being different from the first pitch angle and the second pitch angle.

2. The bur of claim 1, wherein said flutes of the first and second sets of flutes alternate with each other around said head.

3. The bur of claim 1, wherein two said flutes that are symmetric relative to each other extend distally forward of the remaining said flutes so that the two said flutes meet to form a distal end tip on said head.

4. The bur of claim 1, wherein two said flutes that are symmetric relative to each other extend distally forward of the remaining said flutes so that the two said flutes meet to form a distal end tip on said head, the two said flutes having cutting edges proximal to said tip that are angled apart from each other around the tip by at least 90°.

5. The bur of claim 1, wherein said flutes are arranged on said head so that for four arcuately adjacent flutes: the first and second adjacent said flutes are spaced apart by the first pitch angle; the second and third adjacent flutes are spaced apart the second pitch angle; and the third and fourth adjacent flutes are spaced apart the third pitch angle.

6. The bur of claim 1, wherein said flutes of at least one of the flutes sets have a rake angle of 0° or less.

7. The bur of claim 1, wherein said shaft feature for coupling said bur to the surgical bur includes at least one indentation or tab on said shaft.

8. The bur of claim 1, wherein said flutes are arranged on said head so that, for any three arcuately adjacent flutes, the first and second arcuately adjacent flutes are spaced apart by a pitch angle that is different from the pitch angle the second and third arcuately adjacent flutes are spaced apart from each other.

9. The bur of claim 1, wherein said flutes are arranged on said head so that for three pairs of arcuately adjacent pairs of flutes two of the said pairs of said flutes consist of flutes that are spaced apart from each other by the same pitch angle.

10. A bur for use with a surgical tool, said bur having:
- a shaft, said shaft formed with at least one feature to facilitate the coupling of the bur to a surgical tool capable of rotating said shaft and a distal end;
- a head located forward of the distal end of said shaft, said head formed with a plurality of flutes each said flute having: a rake surface with a rake angle; and a clearance surface, said plurality of flutes including:
  - a first set of flutes, each flute of said first set of flutes shaped to have a relief surface that extends between the clearance surface and the rake surface, and a cutting edge where the relief surface and rake surface meet; and
  - a second set of flutes shaped to have rake surfaces and clearance surfaces that meet to form flute cutting edges,
  - wherein, said flutes are arranged on said head so that: said flutes forming a first pair of arcuately adjacent flutes are spaced apart by a first pitch angle; said flutes forming a second pair of arcuately adjacent flutes are spaced apart by a second pitch angle different from the first pitch angle; and said flutes forming a third pair of arcuately adjacent flutes are spaced apart by a third pitch angle, the third pitch angle being different from the first pitch angle and the second pitch angle.

11. The bur of claim 10, wherein said flutes are arranged on said head so that for four arcuately adjacent flutes: the first and second adjacent said flutes are spaced apart by the first pitch angle; the second and third adjacent flutes are spaced apart the second pitch angle; the third and fourth adjacent flutes are spaced apart the third pitch angle.

12. The bur of claim 10, wherein at least some of said flutes have rake angles of 0° or less.

13. The bur of claim 10, wherein two said flutes that are symmetric relative to each other extend distally forward of the remaining said flutes so that the two said flutes meet to form a distal end tip on said head.

14. The bur of claim 10, wherein two said flutes that are symmetric relative to each other extend distally forward of the remaining said flutes so that the two said flutes meet to form a distal end tip on said head, the two said flutes having cutting edges proximal to said tip that are angled apart from each other around the tip by at least 90°.

15. The bur of claim 10, wherein said shaft feature for coupling said bur to the surgical bur includes at least one indentation or tab on said shaft.

16. The bur of claim 10, wherein said flutes of the first and second sets of flutes alternate with each other around said head.

17. The bur of claim 10, wherein said head is formed so that a first group of flutes have a first rake angle and a second group of flutes have a second rake angle that is different from the first rake angle.

18. The bur of claim 10, wherein:
- the first set of flutes has a first rake angle; and
- the second set of flutes have a second rake angle that is different from the first rake angle.

19. The bur of claim 18, wherein the second rake angle is more negative than the first rake angle.

20. The bur of claim 10, wherein said flutes are arranged on said head so that, for any three arcuately adjacent flutes, the first and second arcuately adjacent flutes are spaced apart by a pitch angle that is different from the pitch angle the second and third arcuately adjacent flutes are spaced apart from each other.

21. The bur of claim 10, wherein said flutes are arranged on said head so that for three pairs of arcuately adjacent pairs of flutes two of the said pairs of said flutes consist of flutes that are spaced apart from each other by the same pitch angle.

22. The bur of claim 10, wherein said head is formed to have eight said flutes.

23. The bur of claim 10, wherein said head has a shape of one consisting from the group of: acorn; spherical; cylindrical; conical; and frusto-conical.

24. The bur of claim 1, wherein said head is formed to have eight said flutes.

25. The bur of claim 1, wherein said head has a shape of one consisting from the group of: acorn; spherical; cylindrical; conical; and frusto-conical.

* * * * *